United States Patent
Donello et al.

(10) Patent No.: US 8,173,683 B2
(45) Date of Patent: May 8, 2012

(54) METHODS FOR TREATING COGNITIVE DISORDERS

(75) Inventors: John E. Donello, Dana Point, CA (US); Fabien J. Schweighoffer, Val-de-marne (FR); Lauren M. Luhrs, Rancho Santa Margarita, CA (US)

(73) Assignees: Allergan, Inc., Irvine, CA (US); ExonHit Therapeutics SA, Paris (FR)

( * ) Notice: Subject to any disclaimer, the term of this patent is extended or adjusted under 35 U.S.C. 154(b) by 37 days.

(21) Appl. No.: 12/530,156

(22) PCT Filed: Feb. 26, 2008

(86) PCT No.: PCT/US2008/054935
§ 371 (c)(1),
(2), (4) Date: Oct. 28, 2009

(87) PCT Pub. No.: WO2008/109285
PCT Pub. Date: Sep. 12, 2008

(65) Prior Publication Data
US 2010/0048642 A1   Feb. 25, 2010

Related U.S. Application Data

(60) Provisional application No. 60/893,199, filed on Mar. 6, 2007.

(51) Int. Cl.
*A61K 31/4412* (2006.01)
*C07D 401/06* (2006.01)

(52) U.S. Cl. ............. 514/343; 546/268.1; 546/276.4; 546/279.1; 514/336; 514/340

(58) Field of Classification Search ............ 546/268.1, 546/276.4, 279.1; 514/336, 340, 343
See application file for complete search history.

(56) References Cited

U.S. PATENT DOCUMENTS

| | | | |
|---|---|---|---|
| 5,945,442 | A | 8/1999 | Shayman et al. |
| 5,952,370 | A | 9/1999 | Shayman et al. |
| 6,030,995 | A | 2/2000 | Shayman et al. |
| 6,051,598 | A | 4/2000 | Shayman et al. |
| 6,335,444 | B1 | 1/2002 | Jinbo |
| 8,013,000 | B2 * | 9/2011 | Leblond et al. ............. 514/343 |
| 2002/0115667 | A1 | 8/2002 | Walkley |
| 2003/0050299 | A1 | 3/2003 | Hirth et al. |
| 2003/0153768 | A1 | 8/2003 | Hirth |
| 2005/0101674 | A1 | 5/2005 | Maurer |

FOREIGN PATENT DOCUMENTS

| | | |
|---|---|---|
| JP | 62 114946 | 5/1987 |
| WO | WO 01/38228 | 5/2001 |
| WO | WO 03 008399 | 1/2003 |
| WO | 2006-081273 | 8/2006 |
| WO | WO 2006 018280 | 8/2006 |
| WO | WO 2006 081273 | 8/2006 |
| WO | WO 2008 011483 | 1/2008 |
| WO | WO 2008 011485 | 1/2008 |

OTHER PUBLICATIONS

Yamagishi et al, "A synthetic . . . ", Euro. Journal of Pharm. vol. 462, No. 1-3, 2003, pp. 53-60.
Schneider et al, "The synthetic . . . ", Brain Research, vol. 1099, No. 1, 2006, pp. 199-205.
The Merck Manual of Diagnosis and Therapy, 18th Edition, 2006, pp. 1781,1789, 1808 and 1822.
Shin, S. et al., Tetrahedron asymmetry, 11, 3293-3301, 2000.
Kurosawa et al, Journal of Labelled Compounds & Radiopharmaceuticals (1996), 38(3), 285-97.
Kastron et al. Latvijas PSR Zinatnu Akademijas Vestis, Kimijas Serija (1965) (4), 474-7.

* cited by examiner

*Primary Examiner* — Golam M M Shameem
(74) *Attorney, Agent, or Firm* — Joel B. German; Krishna G. Banerjee

(57) ABSTRACT

Disclosed herein are methods of treating a patient suffering a cognitive disorder.

2 Claims, No Drawings

METHODS FOR TREATING COGNITIVE DISORDERS

CROSS REFERENCE TO RELATED APPLICATIONS

This application is based on, and claims the benefit of, U.S. Provisional Application No. 60/893,199, filed Mar. 6, 2007, and which is incorporated herein by reference.

BACKGROUND OF THE INVENTION

The present invention is directed to methods of treating a patient suffering from one or more types of cognitive disorders.

Several compounds falling within one or more of the general definitions as "derivatives of 3-aryl-3-hydroxy-2-amino-propionic acid amides, of 3-heteroaryl-3-hydroxy-2-amino-propionic acid amides, of 1-aryl-1-hydroxy-2,3-diamino-propyl amines, 1-heteroaryl-1-hydroxy-2,3-diamino-propyl amines" are known in the patent and scientific literature.

For example, United States patent application Publications US 2003/0153768; US 2003/0050299 disclose several examples of the above-mentioned known compounds.

Illustrative specific examples of compounds of these references are shown below:

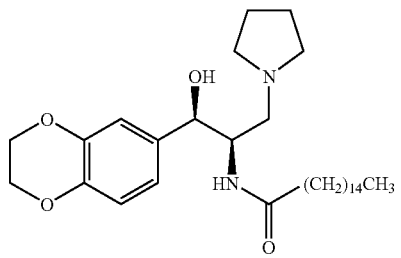

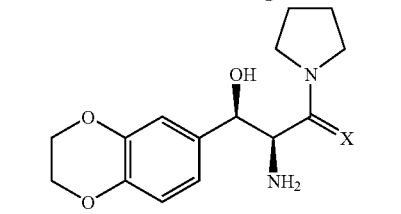

X = H,H
X = O

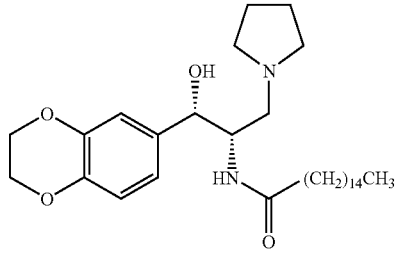

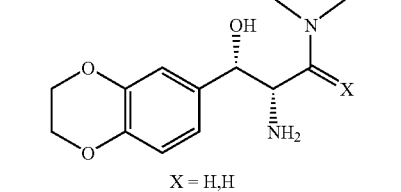

X = H,H
X = O

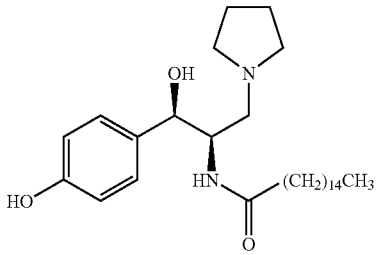

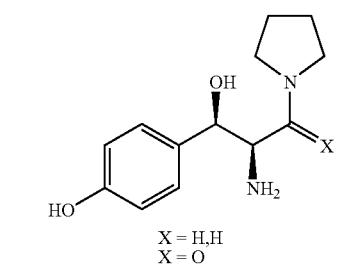

X = H,H
X = O

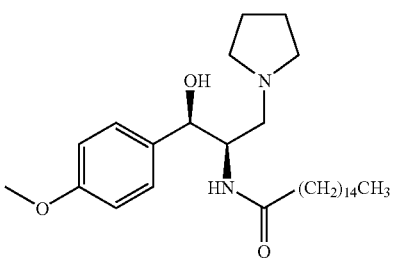

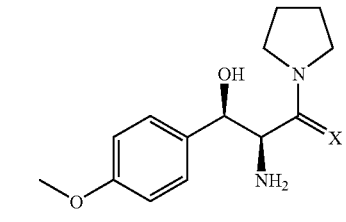

X = H,H
X = O

The publication Shin et al. *Tetrahedron Asymmetry*, 2000, 11, 3293-3301 discloses the following compounds:

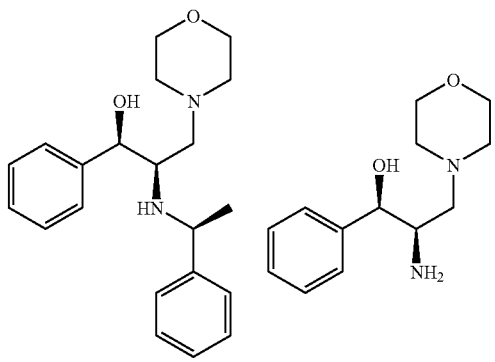

(1R, 2R)-2-((S)-1-phenylethylamino)-3-morpholino-1-phenylpropan-1-ol (1R, 2R)-2-amino-3-morpholino-1-phenylpropan-1-ol -continued

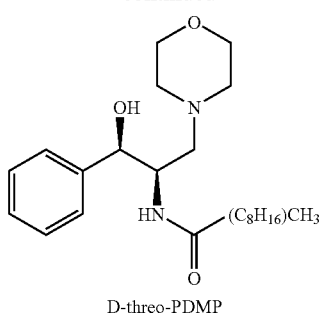

D-threo-PDMP

L-threo-PDMP and some other known compounds used in the methods of this invention are commercially available, in pure enantiomeric and racemic forms, as applicable, from Matreya, LLC Pleasant Gap, Pa.

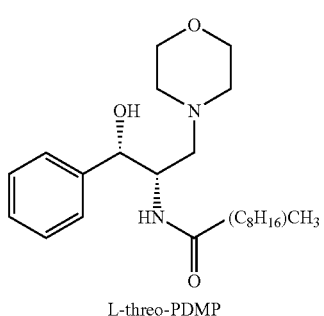

L-threo-PDMP

U.S. Pat. Nos. 5,945,442; 5,952,370; 6,030,995 and 6,051,598, which are all related to each other as being based on same or related disclosures, describe compounds which are structurally similar to the known compounds shown above.

A publication in Kurosawa et al, Journal of Labelled Compounds & Radiopharmaceuticals (1996), 38(3), 285-97 discloses the compound of the formula

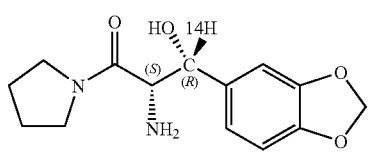

Published PCT application WO 01/38228 discloses

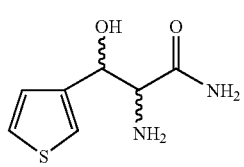

in connection with a chromatographic method.

Kastron et al. in Latvijas PSR Zinatnu Akademijas Vestis, Kimijas Serija (1965) (4), 474-7 disclose the following compound.

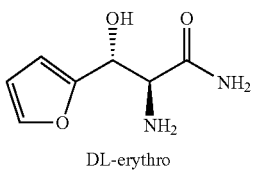

DL-erythro

SUMMARY OF THE INVENTION

The present invention is directed to methods of treating a patient suffering from one or more types of cognitive disorders using the compounds below:

COMPOUND 19

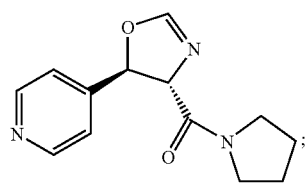

(±)-trans

COMPOUND 50

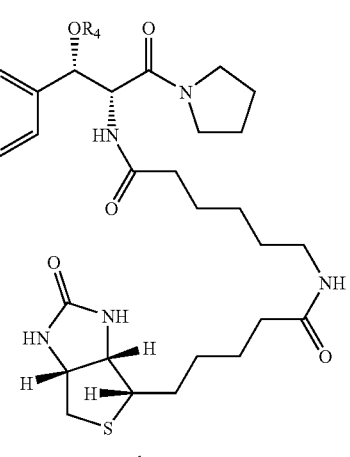

threo

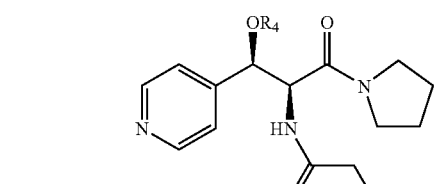

threo

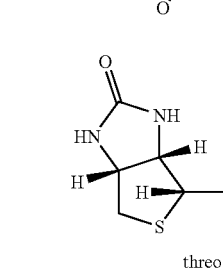

where R4 is H, alkyl of 1 to 6 carbons or CO—R5 where R5 is alkyl of 1 to 6 carbons;

COMPOUND 70

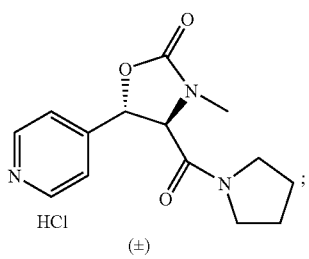

COMPOUND 49

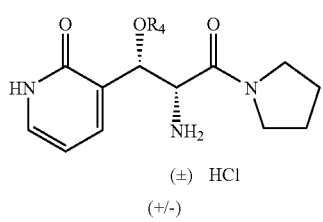

where R4 is H, alkyl of 1 to 6 carbons or CO—R5 where R5 is alkyl of 1 to 6 carbons;

Compound 300

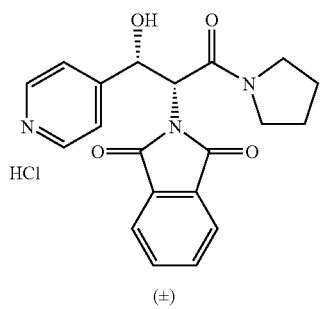

where R4 is H, alkyl of 1 to 6 carbons or CO—R5 where R5 is alkyl of 1 to 6 carbons;

Compound 301

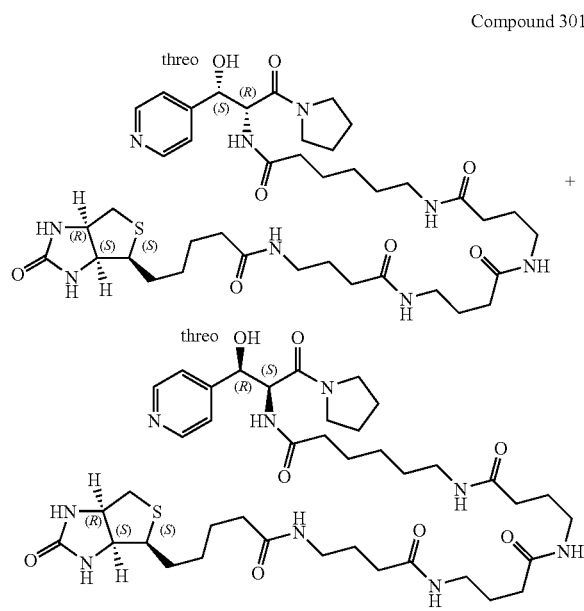

where R4 is H, alkyl of 1 to 6 carbons or CO—R5 where R5 is alkyl of 1 to 6 carbons;

Compound 302

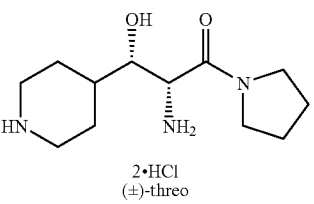

where R4 is H, alkyl of 1 to 6 carbons or CO—R5 where R5 is alkyl of 1 to 6 carbons, and all pharmaceutically acceptable salts of said compounds.

Any of the compounds described here may be used to treat a patient suffering from a cognitive disorder, such as an agnosia, an amnesia, an aphasia, an apraxia, a delirium, a dementia, and a learning disorder.

DETAILED DESCRIPTION OF THE INVENTION

Several compounds of the invention contain one or more asymmetric centers, such that the compounds may exist in enantiomeric as well as in diastereomeric forms. In fact, most of the compounds of the present invention have two asymmetric carbons adjacent to one another and therefore can exist in erythro or threo form, with each of these two forms having dextrorotatory (D) or levorotary (L) enantiomers. Although the threo form is generally preferred in accordance with the present invention unless it is specifically noted otherwise, the scope of the present invention includes all enantiomers, diastereomers and diastereomeric and racemic mixtures. In light of the foregoing, it should be clearly understood that the designation "DL" or "(+/−)" or "(±)" in this application includes the pure dextrorotatory enantiomer, the pure levorotatory enantiomer and all racemic mixtures, including mixtures where the two enantiomers are present in equal or in unequal proportions. Moreover, for simplicity sake in many of the structural formulas, such as in the example below, only one of the enantiomers is actually shown but when the designation "DL" (or "(+/−)" or "(±)") appears it also includes the enantiomeric form (mirror image) of the structure actually shown in the formula.

For example:

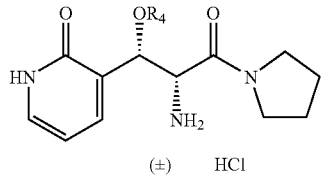

Thus, in the example above, only one enantiomer is shown, but because the designation "DL" (or "(+/−)" or "(±)") appears below the formula, its optical isomer

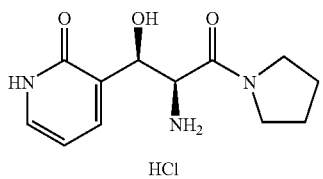

and all racemic mixtures of the two optical isomers are also included.

In the case of some compounds of the present invention one enantiomer of the threo, and in some cases of the erythro, is significantly more active than the other enantiomer of the same pair. For this reason the isolated enantiomer which is significantly more active than the other is considered a novel and inventive composition even if the racemic mixture or one single enantiomer of the same compounds have already been described in the prior art.

Some of the novel compounds of the present invention may contain three or more asymmetric centers.

Keeping the foregoing examples in mind a person of ordinary skill in the art should readily understand the scope of each described example, although in a broad sense all isomers, enantiomers and racemic mixtures are within the scope of the invention.

The term "alkyl" in the general description and definition of the compounds includes straight chain as well as branch-chained alkyl groups.

Generally speaking the compounds of the invention may form salts with pharmaceutically acceptable acids or bases, and such pharmaceutically acceptable salts of the compounds are also within the scope of the invention.

Referring now to the novel compounds of the invention the $R_4$ group shown above and in the claims, is preferably H.

Biological Activity, Modes of Administration

The compounds described here may be used to treat a patient suffering from one or more types of cognitive disorder, such as an agnosia, an amnesia, an aphasia, an apraxia, a delirium, a dementia, and a learning disorder.

To "treat," as used here, means to deal with medically. It includes, for example, administering a compound of the invention to prevent the onset of a cognitive disorder, to alleviate its severity, and to prevent its reoccurrence.

The term "cognitive disorder," as used here, means any condition characterized by a deficit in mental activities associated with thinking, learning, or memory. Examples of such disorders include agnosias, amnesias, aphasias, apraxias, deliriums, dementias, and learning disorders.

In some cases, the cause of a cognitive disorder may be unknown or uncertain. In other cases, the cognitive disorder may be associated with (that is, be caused by or occur in the presence of) other conditions characterized by damage to or loss of neurons or other structures involved in the transmission of signals between neurons. Hence, cognitive disorders may be associated with neurodegenerative diseases such as Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, or senile dementia (Alzheimer type); it may be associated with trauma to the brain, such as that caused by chronic subdural hematoma, concussion, intracerebral hemorrhage, or with other injury to the brain, such as that cause by infection (e.g., encephalitis, meningitis, septicemia) or drug intoxication or abuse.

Cognitive disorders may also be associated with other conditions which impair normal functioning of the central nervous system, including psychiatric disorders such as anxiety disorders, dissociative disorders, mood disorders, schizophrenia, and somatoform and factitious disorders; it may also be associated with conditions of the peripheral nervous system, such as chronic pain.

The compounds described here may be used to treat agnosias, amnesias, aphasias, apraxias, deliriums, dementias, learning disorders and other cognitive disorders regardless of whether their cause is known or not.

Examples of dementias which may be treated with the methods of the invention include AIDS dementia complex, Binswanger's disease, dementia with Lewy Bodies, fronto-temporal dementia, multi-infarct dementia, Pick's disease, semantic dementia, senile dementia, and vascular dementia.

Examples of learning disorders which may be treated with the methods of the invention include Asperger's syndrome, attention deficit disorder, attention deficit hyperactivity disorder, autism, childhood disintegrative disorder, and Rett syndrome.

Examples of aphasia which may be treated with the methods of the invention include progressive non-fluent aphasia.

The compounds described here may also be used to treat patient having deficits in mental activities that are mild or that otherwise do not significantly interfere with daily life. Mild cognitive impairment is an example of such a condition: a patient with mild cognitive impairment displays symptoms of dementia (e.g., difficulties with language or memory) but the severity of these symptoms is such that a diagnosis of dementia may not be appropriate. The compounds described here may be used to treat mild cognitive impairment and other, similarly less severe forms of cognitive disorders.

Examples of Compounds of the Invention

Table 1, below, lists compounds which may be used in the method of the invention.

| Compound | Chemical Formula |
|---|---|
| 19 | 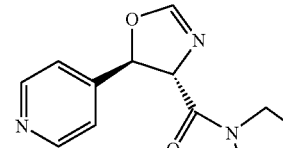 (±)-trans |
| 49 | 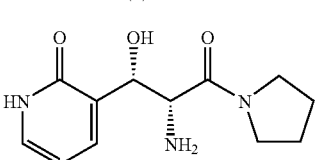 (±)  HCl |

| Compound | Chemical Formula |
|---|---|
| 50 | *threo* |
| | *threo* |
| 70 | HCl (±) |
| 300 | HCl (±)-threo |

Modes of Administration:

The compounds of the invention may be administered at pharmaceutically effective dosages. Such dosages are normally the minimum dose necessary to achieve the desired therapeutic effect; in the treatment of chronic pain, this amount would be roughly that necessary to reduce the discomfort caused by the pain to tolerable levels. For human adults such doses generally will be in the range of 0.1-5,000 mg/day; more preferably in the range of 1 to 3,000 mg/day, 10 mg to 500 mg/day, 500 to 1,000 mg/day, 1,000 to 1,500 mg/day, 1,500 to 2,000 mg/day, 2,000 to 2,500 mg/day, or 2,500 to 3,000 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, intraperitoneal, parenteral, subcutaneous, intranasal, intrathecal, intramuscular, intravenous and intrarectal modes of delivery. Another aspect of the invention is drawn to therapeutic compositions comprising the novel compounds of the invention and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of one or more of the novel or otherwise known compounds of the invention, or of pharmaceutically acceptable salts thereof to a mammal in need thereof. As indicated above, the compound will usually be formulated in a form consistent with the desired mode of delivery.

Synthetic Methods for Obtaining the Compounds of the Invention

The compound of the invention can be synthesized by utilizing the synthetic methods described in the experimental below, or such modifications of the below described experimental methods which will become readily apparent to those skilled in the art in light of the present disclosure. More specifically, the synthesis of each compound of the invention is described for the specific compounds wherein the variable $R_4$ is H. It will be readily understood by those skilled in the art that the compounds wherein the variable $R_4$ is alkyl of 1 to 6 carbons or $CO-R_5$ where $R_5$ is alkyl of 1 to 6 carbons can be readily made by processes well known in the art, such as alkylation or acylation, respectively. It will also be readily understood by those skilled in the art that for the performance of the alkylation or acylation of the hydroxyl group other groups, such as the amino group, may need to be protected and the protective group can be subsequently removed by processes well known in the art. In some cases the alkylation or acylation of the hydroxyl group may be performed on an intermediate in the synthetic process leading to the compounds of the invention.

General

$^1$H NMR spectra were recorded at ambient temperature with an Avance 300 (Bruker) spectrometer. The compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 µm, C18, 4.5×50 mm).

The HPLC method used was a gradient of 5% solvent B to 100% in 7 min. Solvent A was $H_2O$ with 0.05% TFA and solvent B was $CH_3CN$ with 0.05% TFA (Method A).

Melting points were measured with a Büchi B-545 melting point apparatus and were uncorrected. To isolate reaction products the solvent were removed by evaporation using a vacuum rotatory evaporator, the water bath temperature not exceeding 40° C.

General Synthetic Routes

The compound of the invention can be synthesized by utilizing the synthetic methods described in a general sense immediately below and in more detail in the experimental section of the present application, or by such modifications of the below described general and experimental methods which will become readily apparent to those skilled in the art in light of the present disclosure.

Detailed Description of the Synthesis of Preferred Compounds (Experimental)

Preparation of Compound 19

2-Isocyano-1-(pyrrolidin-1-yl)ethanone BLE 04098

To stirred and cooled (0° C.) methyl isocyanoacetate (96% technical grade, 5.0 g, 47.8 mmol) was slowly added in 0.75 h pyrrolidine (6.5 mL, 78 mmol). The mixture was stirred for 1.5 h with continued cooling and then concentrated. The resulting oil was co-evaporated twice from $CH_2Cl_2$:hexane to remove residual pyrrolidine. 2-Isocyano-1-(pyrrolidin-1-yl) ethanone BLE 04098 was obtained as a yellow solid (6.85 g, 98% yield) and used in the next step without purification.

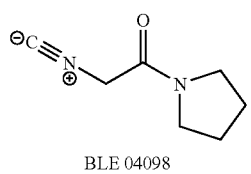

BLE 04098

MW: 138.17; Yield: 98%; yellow solid; Mp (° C.)=73.9.
1H-NMR (CDCl3, δ):: 1.81-2.08 (m, 4H, 2×CH2), 3.35-3.45 (m, 2H, N—CH2), 3.50-3.60 (m, 2H, N—CH2), 4.23 (s, 2H, CH2CO).

General Method B: Exemplified by the preparation of trans-(4,5-dihydro-5-(pyridin-3-yl)oxazol-4-yl) (pyrrolidin-1-yl)methanone BLE 04110B To a stirred and cooled (0° C.) solution of potassium hydroxide (0.55 g, 9.80 mmol) in methanol (10 mL) were added a mixture of 3-pyridine carboxaldehyde (1.03 mL, 10.84 mmol) and 2-isocyano-1-(pyrrolidin-1-yl)ethanone BLE 04098 (1.50 g, 10.86 mmol). The solution was stirred 3 h at 0° C. and then concentrated. The residue was partitioned between ethyl acetate (100 mL) and water. The organic layer was combined with two additional ethyl acetate extracts (2×100 mL), washed with aqueous sodium chloride and dried over MgSO4, filtered and evaporated. Concentration afforded a crude product which was purified by column chromatography on silica ($CH2-Cl_2$:MeOH=98:2) to yield to trans-(4,5-dihydro-5-(pyridin-3-yl)oxazol-4-yl)(pyrrolidin-1-yl) methanone BLE 04110B (0.95 g, 39%) as a pale yellow pale solid.

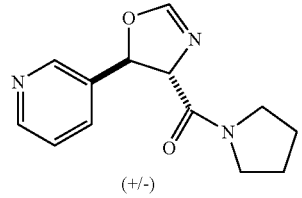

BLE 04110B

MW: 245.28; Yield: 39%; Yellow Pale Solid; Mp (° C.): 107.0.
1H-NMR (CDCl3, δ):: 1.78-2.10 (m, 4H, 2×CH2), 3.40-3.61 (m, 3H, CH2N), 3.90-4.04 (m, 1H, CH2N), 4.59 (dd, 1H, J=7.7 Hz, J=2.2 Hz, CH—N), 6.21 (d, 1H, J=7.7 Hz, CH—O), 7.04 (d, 1H, J=2.2 Hz, O—CH=N), 7.33 (m, 1H, ArH), 7.64 (m, 1H, ArH), 8.59 (d, 2H, J=2.8 Hz, ArH).
$^{13}$C-NMR (CDCl$_3$, δ):: 24.2, 26.0, 46.4, 46.6, 75.7, 79.3, 123.7, 133.5, 135.3, 147.6, 149.9, 155.2, 166.2.

trans-(4,5-Dihydro-5-(pyridin-4-yl)oxazol-4-yl)(pyrrolidin-1-yl)methanone Compound 19

Compound 19 was prepared in accordance with method B using pyridine-4-carbaldehyde (1.88 mL, 19.76 mmol), KOH (1.01 g, 18.00 mmol) in methanol (18 mL) and 2-isocyano-1-(pyrrolidin-1-yl)ethanone BLE 04098 (2.73 g, 19.76 mmol). The residue was partitioned between ethyl acetate (200 mL) and water (150 mL). The organic layer was combined with additional ethyl acetate extracts (2×150 mL), washed with aqueous sodium chloride (2×150 mL) and dried over MgSO4, filtered and evaporated. Trans-(4,5-dihydro-5-(pyridin-4-yl)oxazol-4-yl)(pyrrolidin-1-yl)methanone Compound 19 was obtained as a white solid (4.32 g, 98% yield).

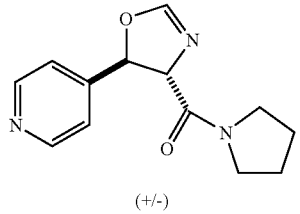

Compound 19

MW: 245.28; Yield: 98%; White Solid; Mp (° C.)=69.2.
$R_f$: 0.65 (MeOH:$CH_2Cl_2$=10:90).
1H-NMR (CDCl3, δ):: 1.78-2.06 (m, 4H, 2×CH2), 3.44-3.60 (m, 3H, CH2N), 3.90-4.01 (m, 1H, CH2N), 4.52 (dd, 1H, J=7.9 Hz, J=2.2 Hz, CH—N), 6.19 (d, J=7.9 Hz, 1H, CH—O), 7.03 (d, 1H, J=2.2 Hz, N=CH—O), 7.24 (dd, 2H, J=4.5 Hz, J=1.5 Hz, ArH), 8.61 (dd, 2H, J=4.5 Hz, J=1.5 Hz, ArH).

Preparation of Compound 50

General Method C: Exemplified by the preparation of DL-threo-2-amino-3-hydroxy-3-(pyridin-3-yl)-1-(pyrrolidin-1-yl)propan-1-one dihydrochloride Compound 20

To a solution of trans-(4,5-dihydro-5-(pyridin-3-yl)oxazol-4-yl)(pyrrolidin-1-yl)methanone BLE 04110B (0.932 g, 3.80 mmol) in MeOH (10 mL) was added hydrochloric acid 37% (1.2 mL). After heating (50° C.) the mixture for 2.25 h the reaction mixture was concentrated and the crude product was coevaporated twice with ethyl acetate. After trituration with ethyl acetate, filtration and drying DL-threo-2-amino-3-hydroxy-3-(pyridin-3-yl)-1-(pyrrolidin-1-yl)propan-1-one dihydrochloride Compound 20 was obtained as a white solid (1.10 g, 94% yield).

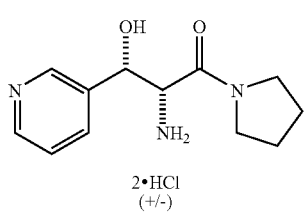

Compound 20

MW: 308.2; Yield: 94%; White Solid; Mp (° C.): 123.4.
1H-NMR (CD$_3$OD, δ):: 1.65-2.00 (m, 4H, 2×CH2), 2.82-3.11 (m, 1H, —CH2N), 3.30-3.57 (m, 2H, C2HN), 3.57-3.77 (m, 1H, CH2N), 4.54 (d, 1H, J=5.3 Hz, CH—N), 5.38 (d, 1H, J=5.3 Hz, CH—O), 8.15 (dd, 1H, J=7.6 Hz, J=5.0 Hz, ArH), 8.68 (d, 1H, J=7.6 Hz, ArH), 8.89 (d, 1H, J=7.6 Hz, ArH), 8.96 (s, 1H, ArH).
$^{13}$C-NMR (CD$_3$OD, δ):: 24.9, 26.9, 47.7, 48.2, 58.1, 69.6, 128.7, 141.5, 141.6, 143.1, 146.5, 165.4.

DL-threo-2-Amino-3-hydroxy-3-(pyridin-4-yl)-1-(pyrrolidin-1-yl)propan-1-one dihydrochloride Compound 22

Compound 22 was prepared following method C with trans-(4,5-dihydro-5-(pyridin-4-yl)oxazol-4-yl)(pyrrolidin-1-yl)methanone Compound 19 (0.750 g, 3.07 mmol), hydrochloric acid 37% (1.0 mL) and methanol (10 mL). After 3.0 h at 50° C. and work-up DL-threo-2-amino-3-hydroxy-3-(pyridin-4-yl)-1-(pyrrolidin-1-yl)propan-1-one dihydrochloride Compound 22 was obtained as a white solid (0.935 g, 99% yield).

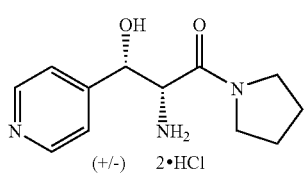

Compound 22

MW: 308.28; Yield: 99%; White Solid; Mp (° C.): 117.0.
1H-NMR (CD3OD, δ):: 1.75-2.03 (m, 4H, 2×CH2), 2.93-3.08 (m, 1H, CH—N), 3.32-3.75 (m, 3H, 2×CH2), 4.54 (d, 1H, J=5.9 Hz, CH—N), 5.40 (d, 1H, J=5.9 Hz, CH—O), 8.21 (d, 2H, J=5.8 Hz, ArH), 8.94 (d, 2H, J=5.8 Hz, ArH).
MS-ESI m/z (% rel. int.): 236.1 ([MH]$^+$, 17), 219 (25), 148 (100).
HPLC: Method A, detection UV 254 nm, Compound 22 RT=0.8 min, peak area 96.3%.

tert-Butyl 5-(DL-threo-1-hydroxy-3-oxo-1-(pyridin-4-yl)-3-(pyrrolidin-1-yl)propan-2-ylcarbamoyl)pentylcarbamate EBE 06102

To a suspension of DL-threo-2-amino-3-hydroxy-3-(pyridin-4-yl)-1-(pyrrolidin-1-yl)propan-1-one dihydrochloride Compound 22 (0.60 g, 1.77 mmol) in CH$_2$Cl$_2$ (12 mL) was added TEA (0.739 mL, 5.32 mmol) and the reaction mixture was stirred for 10 min and cooled in an ice bath with continuous stirring. A solution of Boc-aminohexanoic acid (0.451 g, 1.951 mmol) and BOP (1.05 g, 1.95 mmol) was pre-prepared in CH2Cl2 and added dropwise for 5 min. The reaction mixture was stirred for 2 h at 0° C. and 16 h at RT. After evaporation of the volatiles, the residue was dissolved in EtOAc, washed with NaH2PO4 pH 7.2, saturated NaHCO3, dried over Na2SO4. The resulting white solid was purified by column chromatography on silica gel with 10% EtOAc in EtOAc to give tert-butyl 5-(DL-threo-1-hydroxy-3-oxo-1-(pyridin-4-yl)-3-(pyrrolidin-1-yl)propan-2-ylcarbamoyl)pentylcarbamate EBE 06102 (0.41 g, 52% yield) as a white solid.

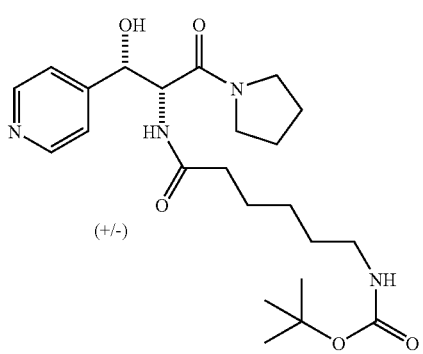

EBE 06102

MW: 448.56; Yield: 52.0%; White Solid.
R$_f$: 0.10 (EtOAc:MeOH=90:10).
1H-NMR: (CDCl3, δ):: 1.10-1.12 (m, 2H, CH2), 1.35-1.55 (m, 11H, (CH3)3 & CH2), 1.72-1.92 (m, 4H, CH2), 2.05-2.22 (m, 2H, CH2), 2.40 (d, 2H, J=9.3 Hz, CH2), 3.05 (q, 2H, J=6.6 Hz, CH2), 3.20-3.28 (m, 1H, NCH2), 3.32-3.50 (m, 2H, NCH2), 3.62-3.72 (m, 1H, NCH2), 4.79 (bs, 1H, NH), 4.97 (dd, 1H, J=8.7, 4.1 Hz, NCH), 5.07 (d, 1H, J=4.1 Hz, OCH), 5.40 (bs, 1H, NH), 6.74 (d, 1H, J=8.4 Hz, OH), 7.35 (d, 2H, J=6.0 Hz, ArH), 8.56 (d, 2H, J=6.0 Hz, ArH).
$^{13}$C-NMR (CDCl$_3$, δ):: 24.0, 25.0, 26.1, 28.4, 29.6, 35.9, 36.9, 40.3, 46.1, 46.9, 54.9, 72.9, 79.0, 121.3, 148.8, 149.6, 156.1, 169.0, 173.2.
MS-ESI m/z (% rel. Int.): 449.1 ([MH]$^+$, 20).
HPLC: Method A, detection UV 254 nm, EBE 06102 RT=4.1 min, peak area 99.9%.

6-(5-((3aR,6S,6aS)-hexahydro-2-oxo-1H-thieno[3,4-d]imidazol-6-yl)pentanamido)-N-((1R,2S)- & (1S,2R)-1-hydroxy-3-oxo-1-(pyridin-4-yl)-3-(pyrrolidin-1-yl)propan-2-yl)hexanamides Compound 50

To a solution of 5-(DL-threo-1-hydroxy-3-oxo-1-(pyridin-4-yl)-3-(pyrrolidin-1-yl)propan-2-ylcarbamoyl)pentylcarbamate EBE 06102 (0.370 g, 0.824 mmol), in MeOH (1 mL) was added a solution of HCl (4.2 M) in EtOAc (10 mL). The reaction mixture was stirred for 2 h at RT and the volatiles were evaporated to yield a crude brown oil EBE 06104 (0.221 g, 63% crude yield) that was used without purification in the next step. To a suspension of EBE 06104 (0.221 g, 0.522 mmol) in CH2Cl2 (5 mL) was added triethylamine (0.217 mL, 1.57 mmol) and the reaction mixture was stirred for 10 min and cooled in an ice bath with continuous stirring. A solution of biotin (0.14 g, 0.574 mmol) and BOP (0.309 g, 0.574 mmol) was pre-prepared in CH2Cl2 (1 mL) and added dropwise for 5 min. The mixture was stirred for 2 h at 0° C. and 16 h at RT. The reaction mixture was evaporated to dryness, partitioned between NaH2PO4 and n-Butanol. The n-butanol phase was washed with saturated Na2CO3 and evaporated to dryness. The desired product was isolated using column chromatography (EtOAc:MeOH:NH4OH=70:28:2) to give Compound 50 (diastereoisomeric mixture in ratio 1:1, 0.160 g, 53% yield) as a white solid.

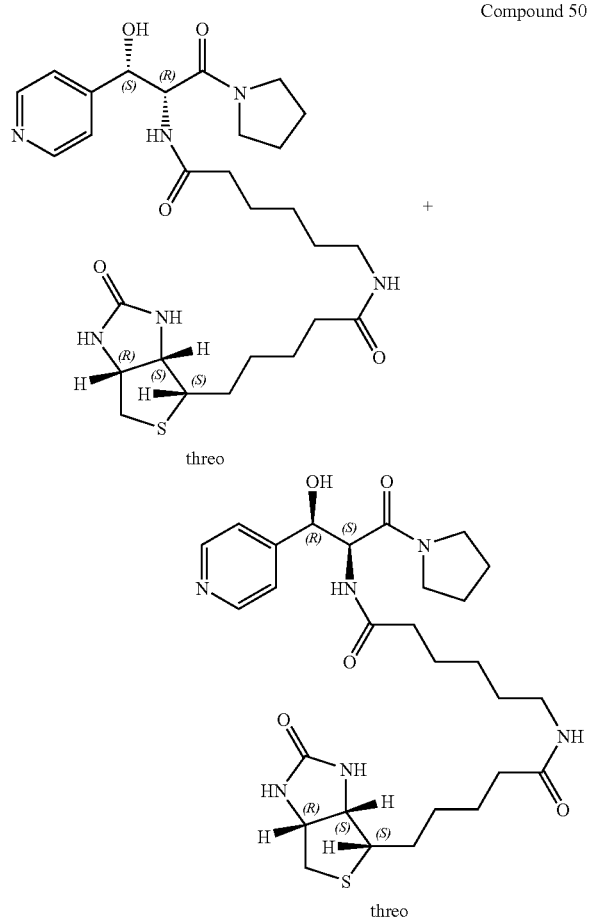

Compound 50 threo threo

MW: 574.74; Yield: 53%; White Solid; Mp (° C.): 64.3.
$R_f$: 0.2 (EtOAc:MeOH:NH4OH=70:28:2).

1H-NMR (CDCl3, δ):: 1.17-1.32 (m, 2H), 1.40-1.60 (m, 4H), 1.60-1.90 (m, 6H), 1.90-2.10 (m, 4H), 2.15-2.30 (m, 4H), 2.74 (d, 1H, J=12.6 Hz), 2.91 (dd, J=4.8 Hz, 12.8 Hz), 2.95-3.10 (m, 1H), 3.10-3.45 (m, 4H), 3.60-3.72 (m, 1H), 4.34 (dd, 1H J=4.4 Hz J=7.5 Hz), 4.50-4.58 (m, 1H), 4.85-4.95 (m, 1H), 5.02-5.08 (m, 1H), 6.12 (s, 1H), 6.50-6.15 (m, 1H), 6.68 (s, 1H), 7.36 (m, 2H), 7.67 (q, 1H, J=8.12 Hz), 8.55 (d, 2H, J=5.8 Hz).

MS-ESI m/z (% rel. Int.): 575.3 ([MH]$^+$, 70).

HPLC: Method A, detection UV 254 nm, Compound 50 RT=3.61 min, peak area 97.2%.

Preparation of Compound 49 trans-(4,5-Dihydro-5-(2-methoxypyridin-3-yl)oxazol-4-yl)(pyrrolidin-1-yl)methanone BAL 01014

BAL 01014 was prepared in accordance with method D using 2-methoxy-3-pyridinecarboxaldehyde (0.64 ml, 5.43 mmol), KOH (0.305 mg, 5.43 mmol) in methanol (5 mL) and 2-isocyano-1-(pyrrolidin-1-yl)ethanone BLE 04098 (0.75 g, 5.43 mmol). After work-up trans-(4,5-dihydro-5-(2-methoxypyridin-3-yl)oxazol-4-yl)(pyrrolidin-1-yl)methanone BAL 01014 was obtained (0.74 mg, 50% yield) as a white solid.

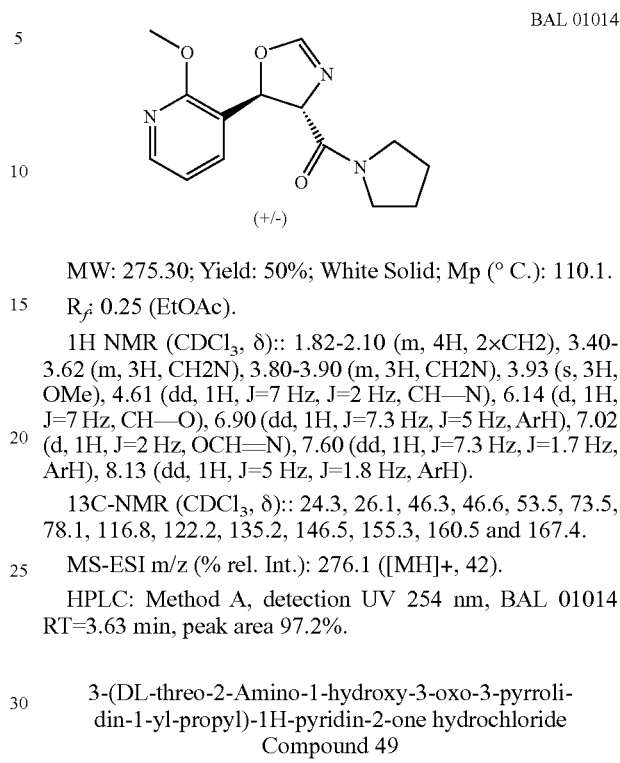

BAL 01014

(+/-)

MW: 275.30; Yield: 50%; White Solid; Mp (° C.): 110.1.
$R_f$: 0.25 (EtOAc).

1H NMR (CDCl3, δ):: 1.82-2.10 (m, 4H, 2×CH2), 3.40-3.62 (m, 3H, CH2N), 3.80-3.90 (m, 3H, CH2N), 3.93 (s, 3H, OMe), 4.61 (dd, 1H, J=7 Hz, J=2 Hz, CH—N), 6.14 (d, 1H, J=7 Hz, CH—O), 6.90 (dd, 1H, J=7.3 Hz, J=5 Hz, ArH), 7.02 (d, 1H, J=2 Hz, OCH=N), 7.60 (dd, 1H, J=7.3 Hz, J=1.7 Hz, ArH), 8.13 (dd, 1H, J=5 Hz, J=1.8 Hz, ArH).

13C-NMR (CDCl3, δ):: 24.3, 26.1, 46.3, 46.6, 53.5, 73.5, 78.1, 116.8, 122.2, 135.2, 146.5, 155.3, 160.5 and 167.4.

MS-ESI m/z (% rel. Int.): 276.1 ([MH]+, 42).

HPLC: Method A, detection UV 254 nm, BAL 01014 RT=3.63 min, peak area 97.2%.

3-(DL-threo-2-Amino-1-hydroxy-3-oxo-3-pyrrolidin-1-yl-propyl)-1H-pyridin-2-one hydrochloride Compound 49 trans-(4,5-Dihydro-5-(2-methoxypyridin-3-yl)oxazol-4-yl)(pyrrolidin-1-yl)methanone BAL 01014 (0.684 g, 2.487 mmol) was dissolved in methanol (10 mL). A solution of hydrochloric acid (37%, 0.6 mL) was added via syringe at RT. The mixture was stirred for 22 h at reflux. The residue was concentrated, triturated with EtOAc and filtered to obtain a yellow pale solid 3-(DL-threo-2-amino-1-hydroxy-3-oxo-3-pyrrolidin-1-yl-propyl)-1H-pyridin-2-one hydrochloride Compound 49 (136 mg, 19.0% yield).

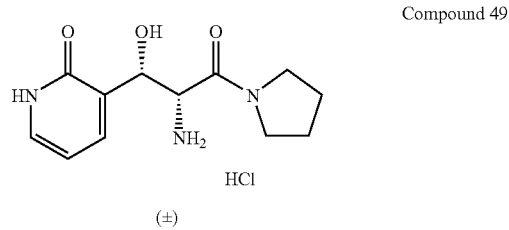

Compound 49

(±)

MW: 287.74; Yield: 19.0%; Yellow Pale Solid; Mp (° C.): 180.

1H NMR (CD3OD, δ):: 1.82-2.09 (m, 4H, CH2), 3.35-3.80 (m, 4H, CH2N), 4.63 (s, 1H, CH—N), 5.17 (s, 1H, CH—O), 6.56 (t, 1H, ArH)), 7.5 (d, 1H, J=6.1 Hz, ArH), 7.86 (d, 1H, J=6.5 Hz, ArH).

$^{13}$C-NMR (CD$_3$OD, δ):: 24.2, 26.0, 46.6, 46.6, 75.8, 79.7, 127.3, 127.5, 127.9, 129.4, 130.0, 132.3, 133.2, 148.1, 148.4, 155.3, 166.2.

MS-ESI m/z (% rel. Int.): 252.1 ([MH]$^+$, 18), 163.0 (100).

HPLC: Method A, detection UV 254 nm, Compound 49 RT=1.13 min, peak area 84.0%.

Preparation of Compound 300

(±)-threo-2-Phthalimide-3-hydroxy-3-(pyridin-4-yl)-1-(pyrrolidin-1-yl)propan-1-one hydrochloride Compound 300

(±)-threo-2-Amino-3-hydroxy-3-(pyridin-4-yl)-1-(pyrrolidin-1-yl)propan-1-one dihydrochloride Compound 22 (0.51 g, 1.64 mmol) was treated by 20 mL of a 1 N aqueous solution of K2CO3 and extracted (5×40 mL) with a mixture CH2Cl2:MeOH=90:10. The solution was dried over MgSO4, filtered and evaporated to obtain the free base of Compound 22 (0.323 g, 82.5% yield) as a white solid.

In a 10 mL round-bottom flask phthalic anhydride (0.203 mg, 1.373 mmol) was added to the free base of Compound 22 (0.323 g, 1.37 mmol) and the mixture was heated from 65° C. to 145° C. and stirred 5 min at 145° C.

After cooling a yellow black gum was obtained as a crude product. This crude product was purified by column chromatography (SiO2, EtOAc:MeOH=100:0 to 90:10). After evaporation of the solvents, a white solid (±)-threo-2-phthalimide-3-hydroxy-3-(pyridin-4-yl)-1-(pyrrolidin-1-yl)propan-1-one BLE 04156A was obtained as a white solid (0.15 g, 30% yield). To (±)-threo-2-phthalimide-3-hydroxy-3-(pyridin-4-yl)-1-(pyrrolidin-1-yl)propan-1-one BLE 04156A (0.135 g, 0.37 mmol) was added a solution 0.1 N of HCl in isopropanol (10 mL) and the mixture was evaporated to dryness at 28° C. on a rotavapor then to high vacuum pump. (±)-threo-2-Phthalimide-3-hydroxy-3-(pyridin-4-yl)-1-(pyrrolidin-1-yl)propan-1-one hydrochloride Compound 300 (0.147 g, 24.5% yield) was obtained as a white solid.

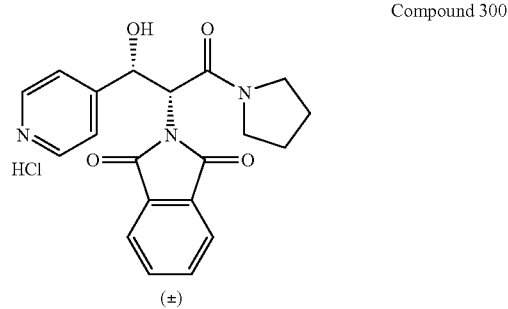

Compound 300

MW: 401.84; Yield: 24.5%; White Solid; Mp (° C.): 201.8.

1H-NMR (CD3OD): 1.60-1.90 (m, 4H, 2×CH2), 2.95-3.09 (m, 1H, CH2N), 3.30-3.47 (m, 3H, CH2N), 5.30 (d, 1H, J=7.9 Hz, CH), 5.82 (d, 1H, J=7.9 Hz, CH), 7.80 (m, 4H, ArH), 8.25 (d, 2H, J=5.4 Hz, ArH), 8.81 (d, 2H, J=5.2 Hz, ArH).

13C-NMR (CD3OD): 24.7, 27.1, 47.7, 47.8, 58.0, 70.6, 124.8 (2×C), 127.5 (2×C), 132.6 (2×C), 136.1 (2×C), 142.5 (2×C), 164.9, 166.5, 168.8.

MS-ESI m/z (% rel. Int.): 366.0 ([MH]+, 22), 219.1 (100), 148.0 (47).

HPLC: Method A, detection UV 254 nm, RT=3.88 min, peak area 98.7%.

Preparation of Compound 301 tert-butyl 5-((±)-threo-1-hydroxy-3-oxo-1-(pyridin-4-yl)-3-(pyrrolidin-1-yl)propan-2-ylcarbamoyl)pentylcarbamate Compound 237

To a solution of N-Boc-aminohexanoic acid (342 mg, 1.48 mmol) in THF (10 mL) was added N-methylmorpholine (163 µL, 1.48 mmol). The solution was stirred for 5 min, cooled at −15° C. and treated dropwise with isobutyl chloroformate (211 µL, 1.48 mmol). This solution was added via a stainless steel cannula to a solution of (±)-threo-2-amino-3-hydroxy-3-(pyridin-4-yl)-1-(pyrrolidin-1-yl)propan-1-one dihydrochloride Compound 22 (500 mg, 1.48 mmol) and N-methylmorpholine (489 mg, 1.47 mmol) in THF (10 mL) at −15° C. The reaction mixture was kept for 0.5 h at −15° C. followed by 2 h at 25° C. with continuous stirring. After evaporation of the solvent, the residue was partitioned between EtOAc and H2O, washed with NaH2PO4, saturated aqueous NaHCO3, dried over sodium sulfate and purified by column chromatography (SiO2) with a gradient of 0% to 10% [v/v] MeOH in EtOAc to give tert-butyl 5-((±)-threo-1-hydroxy-3-oxo-1-(pyridin-4-yl)-3-(pyrrolidin-1-yl)propan-2-ylcarbamoyl)pentylcarbamate Compound 237 (455 mg, 69% yield) as a white solid.

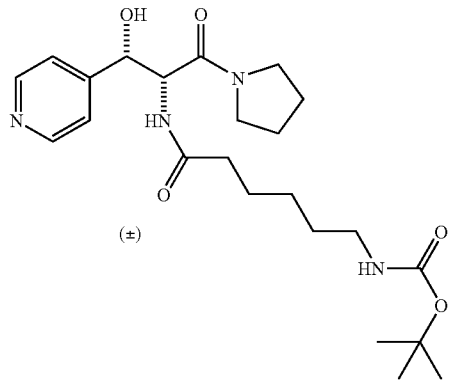

Compound 237

MW: 448.6; Yield: 69%; White Solid.

R$_f$: 0.20 (EtOAc:MeOH=90:10).

1H-NMR (CD3OD, δ): 1.05-1.15 (m, 2H, CH2), 1.35-1.55 (m, 13H, 2×CH2+C(CH3)3), 1.75-1.95 (m, 4H, 2×CH2), 2.00-2.20 (m, 2H, O=CCH2), 3.05 (q, 2H, J=6.7 Hz, N—CH2), 3.20-3.35 (m, 1H, N—CH), 3.38-3.50 (m, 2H, N—CH2), 3.65-3.75 (m, 1H, N—CH), 4.72 (bs, 1H, NH), 4.98 (dd, 1H, J=8.8 Hz, J=3.6 Hz), 5.08 (d, 1H, J=3.3 Hz, OCH), 5.23 (bs, 1H, OH), 6.50 (d, 1H, J=8.7 Hz, NH), 7.35 (d, 2H, J=6.0 Hz, ArH), 8.58 (d, 2H, J=4.6 Hz, J=1.4 Hz, ArH).

MS-ESI m/z (% rel. Int.): 449.2 ([MH]+, 30), 349.2 (100).

HPLC: Method A, detection at 254 nm, RT=4.03 min, peak area 99.9%.

6-Amino-N-((±)-threo-1-hydroxy-3-oxo-1-(pyridin-4-yl)-3-(pyrrolidin-1-yl)propan-2-yl)hexanamide Compound 238

To a solution of tert-butyl 5-((±)-threo-1-hydroxy-3-oxo-1-(pyridin-4-yl)-3-(pyrrolidin-1-yl)propan-2-ylcarbamoyl)pentylcarbamate Compound 237 (81 mg, 0.181 mmol) in CH2Cl2 (8 mL) was added TFA (2 mL) at 0° C. and stirred for 2 h at 0° C. All the volatiles were evaporated to give a residue that was treated with a suspension of Amberlite-400 (OH—) in MeOH. After filtration, the filtrate was evaporated and the product was isolated by column chromatography (SiO2) with CH2Cl2:MeOH:NH4OH=10:5:0.4 to afford 6-amino-N-((±)-threo-1-hydroxy-3-oxo-1-(pyridin-4-yl)-3-(pyrrolidin-1-yl)propan-2-yl) hexanamide Compound 238 (40 mg, 64% yield) as a white solid.

Compound 238

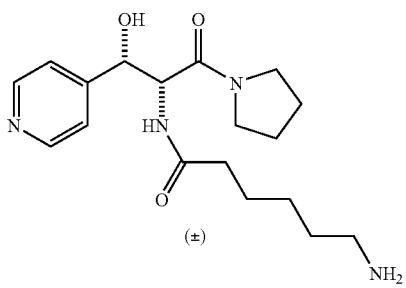

(±)

MW: 448.6; Yield: 64%; White Solid; Mp (° C.): 134.4.
R$_f$: 0.30 (CH2Cl2:MeOH:NH4OH=10:5:0.4).
1H NMR (CDCl3, δ): 1.12-1.30 (m, 2H, CH2), 1.30-1.50 (m, 2H, CH2), 1.50-1.65 (m, 2H, CH2), 1.65-1.95 (m, 4H, CH2), 2.10-2.30 (m, 2H, CH2), 2.55-2.70 (t, 2H, J=6.9 Hz, CH2), 3.10-3.20 (m, 2H, CH2), 3.28-3.50 (m, 2H, CH2), 3.60-3.70 (m, 1H, CH), 4.95 (dd, 1H, J=5.1 Hz, J=8.4 Hz, O—CH), 5.02 (d, 1H, J=5.0 Hz, OH), 7.11 Hz (d, J=8.48 Hz, 1H, ArH), 7.35 (dd, 2H, J=4.4 Hz, J=1.5 Hz, ArH), 8.55 (dd, J=1.5 Hz, J=4.6 Hz, 2H, ArH).
$^{13}$C NMR (CDCl$_3$, δ): 24.0, 25.1, 25.8, 25.9, 32.5, 35.8, 41.7, 46.0, 46.9, 55.6, 72.6, 121.3 (2×C), 149.2, 149.5 (2×C), 168.9, 173.7.

(±)-threo-{3-[3-(3-{5-[1-(Hydroxy-pyridin-4-yl-methyl)-2-oxo-2-pyrrolidin-1-yl-ethylcarbamoyl]-pentylcarbamoyl}-propylcarbamoyl)-propylcarbamoyl]-propyl}-carbamic acid tert-butyl ester TTA 08156

Boc-GABA-GABA-GABA-OH (354 mg, 0.95 mmol) was stirred in CHCl3 (40 mL) with Et3N (0.3 mL, 2.1 mmol) and HOBT (145 mg, 1.05 mmol) at 4° C. for 5 min under nitrogen. EDC (205 mg, 1.05 mmol) was added and the mixture was stirred for 15 min at 4° C. 6-Amino-N-((±)-threo-1-hydroxy-3-oxo-1-(pyridin-4-yl)-3-(pyrrolidin-1-yl)propan-2-yl)hexanamide (333 mg, 0.95 mmol) in CHCl3 (20 mL) was added dropwise and the mixture was stirred at 4° C. for 2 h and 15 h at RT under nitrogen. Brine (30 mL) was added and the product was extracted by CH2Cl2 (200 mL). The organic layer was washed with a solution of 2 N NaOH, brine and dried over MgSO4. After filtration the solution was evaporated and dried to give a crude yellow oil (420 mg). After purification by column chromatography (SiO2, CH2Cl2:MeOH=85:15) (±)-threo-{3-[3-(3-{5-[1-(hydroxy-pyridin-4-yl-methyl)-2-oxo-2-pyrrolidin-1-yl-ethylcarbamoyl]-pentylcarbamoyl}-propylcarbamoyl)-propylcarbamoyl]-propyl}-carbamic acid tert-butyl ester TTA 08156 (260 mg, 39% yield) was obtained as a pale yellow oil.

MW: 703.87; Yield: 39%; Pale Yellow Oil.
R$_f$: 0.20 (CH2Cl2:MeOH=9:1).
1H-NMR (CDCl$_3$, δ): 1.17-1.25 (m, 2H, CH$_2$), 1.40-1.56 (m, 13H, 2×CH$_2$, 3×CH3) 1.73-1.85 (m, 10H, 5×CH$_2$), 2.13-2.29 (m, 8H, 4×CH$_2$CO), 2.40 (s, 1H, OH), 3.09-3.67 (m, 12H, 6×CH$_2$—N), 4.91 (dd, 1H, J=4.9 Hz, J=8.5 Hz, CH—N), 5.05 (d, 1H, J=5.1 Hz, CH—O), 5.15 (t, 1H, J=5.8 Hz, NH), 7.01-7.04 (m, 1H, NH), 7.14 (t, 1H, J=5.6 Hz, NH), 7.33 (t, 1H, J=5.6 Hz, NH), 7.37 (d, 2H, J=6.0 Hz, ArH), 8.55 (d, 2H, J=6.0 Hz, ArH).
13C-NMR (CD$_3$OD, δ): 24.0, 24.9, 25.6, 25.8, 26.1, 26.5, 28.4 (3×C), 29.0, 33.5, 33.7, 35.8, 38.6, 38.8, 39.1, 39.6, 46.1, 46.8, 55.6, 72.7, 79.5, 121.5 (×2), 149.1, 149.5 (×2), 156.7, 168.8, 173.1, 173.3, 173.4, 173.5.
MS-ESI m/z (% rel. Int.): 704.3 ([MH]$^+$, 100).
HPLC: Method A, detection UV 254 nm, TTA 08156 RT=3.90 min, peak area 99.0%.

6-(5-((3aR,6S,6aS)-hexahydro-2-oxo-1H-thieno[3,4-d]imidazol-6-yl)-pentanoylamino)-butyrylamino-butyrylamino -butyrylamino-N-((1R,2S)-& (1S,2R)-1-hydroxy-3-oxo-1-(pyridin-4-yl)-3-(pyrrolidin-1-yl)propan-2-yl) hexanamides Compound 301.

(±)-threo-{3-[3-(3-{5-[1-(Hydroxy-pyridin-4-yl-methyl)-2-oxo-2-pyrrolidin-1-yl-ethylcarbamoyl]-pentylcarbamoyl}-propylcarbamoyl)-propylcarbamoyl]-propyl}-carbamic acid tert-butyl ester TTA 08156 (260 mg, 0.37 mmol) was stirred in MeOH (5 mL) with HCl 37% (0.3 mL, 3.70 mmol) for 15 min at 40° C. MeOH was evaporated and the residue was dried in vacuum. Amberlite IRA-400 (Cl—) (6 mL, 8.4 mmol) was washed successively with water (2×10 mL), NaOH 0.5 N (3×20 mL), water (2×10 mL) and MeOH (3×10 mL). The previously obtained residue and washed Amberlite were stirred in MeOH (30 mL) for 5 min at RT. After filtration, the MeOH was evaporated to give amine in the free base form (210 mg, 94% yield). Biotin (95 mg, 0.38 mmole) was dissolved in a mixture CHCl3/DMF (40 mL/10 mL) and Et3N (0.11 mL, 0.77 mmol), HOBT (53 mg, 0.38 mmol) and EDC (75 mg, 0.38 mmol) were added and the solution stirred at RT for 2 h under nitrogen. The previously obtained amine (210 mg, 0.35 mmol) in CHCl3 (10 mL) was added dropwise and the mixture was stirred for 24 h at RT under nitrogen. Brine (40 mL), 2 N NaOH (10 mL), CHCl3 (50 mL) were added and the product was extracted by 3 additional extractions of a mixture CHCl3/DMF (50 mL/10 mL). The combined organic layer was washed with brine, dried over MgSO4, filtered, evaporated to give crude yellow oil (160 mg, 52% yield). The crude oil was purified by column chromatography (SiO2, CH2Cl2:MeOH:NH3=95:5:0.1 to 85:15:0.3) to obtain after evaporation 6-(5-((3aR,6S,6aS)-hexahydro-2-oxo-1H-thieno[3,4-d]imidazol-6-yl)-pen-

TTA 08156

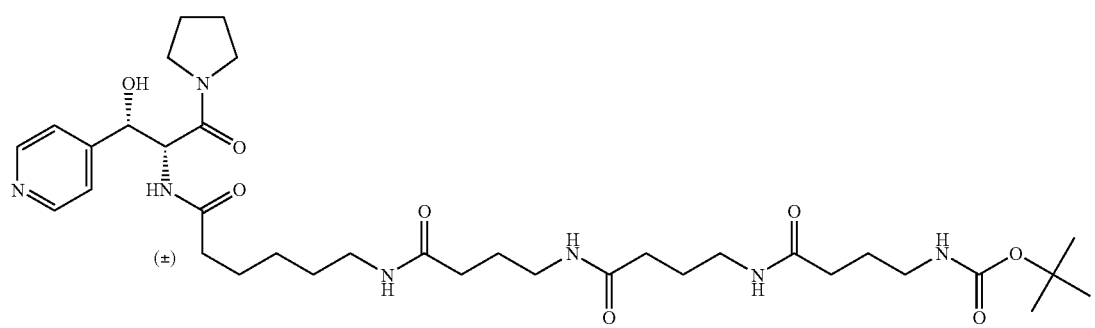

tanoylamino)-butyrylamino-butyrylamino-butyrylamino-N-((1R, 2S)-&(1S,2R)-1-hydroxy-3-oxo-1-(pyridin-4-yl)-3-(pyrrolidin-1-yl)propan-2-yl)hexanamides (diastereoisomeric mixture ratio 1:1) as a pale yellow oil (45 mg, 15% yield).

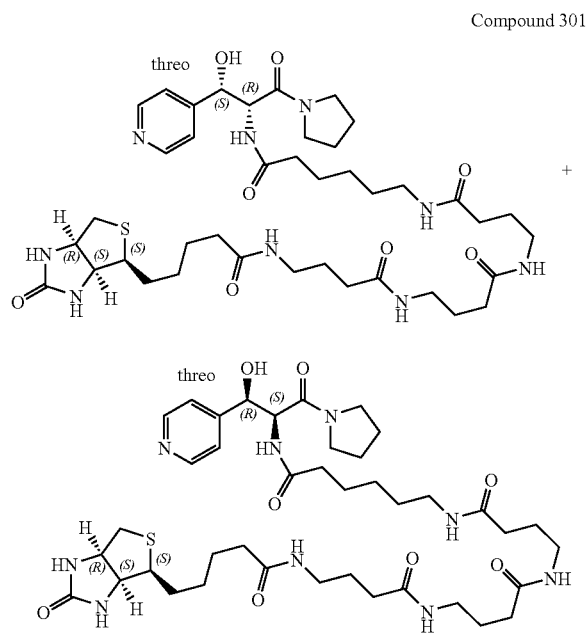

Compound 301

MW: 830.05; Yield: 15%; Pale Yellow Oil.

R$_f$: 0.30 (CH$_2$Cl$_2$:MeOH:NH$_3$=85:15:0.3).

1H-NMR (CD$_3$OD, δ): 1.26-1.82 (m, 22H, 11×CH$_2$), 2.18-2.25 (m, 10H, 5×CH$_2$CO), 2.70 (d, 1H, J=12.7 Hz, CH$_2$—S), 2.92 (dd, 1H, J=4.8 Hz, J=12.7 Hz, CH$_2$S), 3.06-3.80 (m, 13H, 6×CH$_2$—N, CH—S), 4.29 (dd, 1H, J=4.4 Hz, J=7.8 Hz, CH—N), 4.48 (dd, 1H, J=4.9 Hz, J=7.8 Hz, CH—N), 4.82 (d, 1H, J=6.4 Hz, CH—N), 5.01 (d, 1H, J=6.4 Hz, CH—O), 7.49 (d, 2H, J=5.5 Hz, ArH), 8.5 (d, 2H, J=4.6 Hz, ArH).

13C-NMR (CD$_3$OD, δ): 25.0, 26.5, 26.8, (2×C), 26.9 (2×C), 27.5, 29.5, 29.8, 30.1, 34.3, 34.4 (2×C), 36.4, 36.8, 39.8, 39.9, 40.1, 41.1, 47.2, 47.3, 57.1, 58.3, 61.6, 63.4, 73.1, 74.2, 123.5 (2×C), 149.9 (2×C), 152.8, 166.1, 170.0, 175.3, 175.4 (2×C), 176.0, 176.1.

MS-ESI m/z (% rel. Int.): 830.2. ([MH]$^+$, 85), 219.1 (100).

HPLC: Method A, detection UV 254 nm, RT=3.70 min, peak area 99.8%.

Preparation of Compound 302

(±)-threo-2-Amino-3-hydroxy-3-(piperidin-4-yl)-1-(pyrrolidin-1-yl)propan-1-one dihydrochloride Compound 302

(±)-threo-2-Amino-3-hydroxy-3-(pyridin-4-yl)-1-(pyrrolidin-1-yl)propan-1-one dihydrochloride Compound 22 (500 mg, 1.61 mmol) was stirred in AcOH (10 mL) with PtO2 hydrate typical (Pt content 79-84%, 100 mg) under hydrogen at atmospheric pressure for 24 h at RT. After filtration on Celite® 545, the filtrate was evaporated and the residue was dried under vacuum to give a beige solid (450 mg, 88.2% yield). The crude product was stirred in MeOH (50 mL) with Amberlite (Cl—) IRA-400 (9 mL, 12.7 mmol washed beforehand by NaOH 0.5 N then water and MeOH) at RT for 15 min. The mixture was filtered off, the filtrate was evaporated and the free base form was purified by column chromatography (SiO2, CH2Cl2:MeOH:20% NH3 in H2O=70:30:8) to give (±)-threo-2-amino-3-hydroxy-3-(piperidin-4-yl)-1-(pyrrolidin-1-yl)propan-1-one TTA 08144A (226 mg, 58% yield). HCl Treatment in MeOH gave (±)-threo-2-amino-3-hydroxy-3-(piperidin-4-yl)-1-(pyrrolidin-1-yl)propan-1-one dihydrochloride Compound 302 (190 mg, 28% yield) as a white solid.

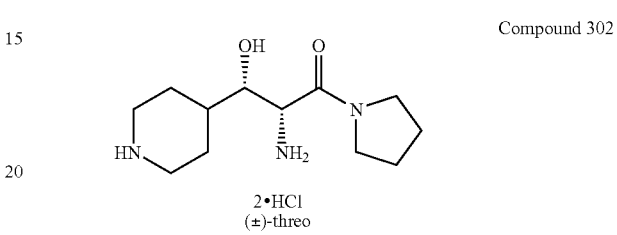

Compound 302

2·HCl
(±)-threo

MW: 314.25; Yield: 28.0%; White Solid; Mp (° C.): 197.5.

R$_f$: 0.20 (CH2Cl2:MeOH:20% NH3 in H2O=70:30:8, free base).

1H-NMR (CD$_3$OD, δ): 1.57-2.00 (m, 9H, 4×CH$_2$ & CH), 2.94-3.08 (m, 2H, CH$_2$—N), 3.46-3.77 (m, 7H, 3×CH$_2$—N, CH—N), 4.33 (s, 1H, CH-0).

13C-NMR (CD$_3$OD, δ): 22.5, 23.4, 24.1, 24.7, 35.2, 42.2, 42.5, 45.4, 45.5, 52.0, 69.8, 164.6.

MS-ESI m/z (% rel. Int.): 242.2 ([MH]$^+$, 45), 129.1 (100).

HPLC: Method A, detection UV 214 nm, RT=0.70 min, peak area 98.0%.

Preparation of Compound 70

Method D (in CH$_2$Cl$_2$):

To a stirred solution of DL-threo-2-amino-3-hydroxy-3-(pyridin-4-yl)-1-(pyrrolidin-1-yl)propan-1-one dihydrochloride Compound 22 (0.15 g, 0.49 mmol) in 10 mL of CH$_2$Cl$_2$ at +4° C. were added triethylamine (200 μl, 1.45 mmol) and very slowly acid chloride in 3 mL of CH$_2$Cl$_2$. The mixture was stirred overnight at RT under nitrogen and then partitioned between CH2Cl2 and 1 N aqueous sodium carbonate. The organic layer was evaporated and the obtained residue purified by column chromatography on silica (EtOAc:MeOH=95:5). The hydrochloride salt was obtained in MeOH at 0° C. with 0.3 M HCl in diethylether to give after evaporation of solvents and drying the acylated compound.

Benzyl DL-threo-3-hydroxy-1-oxo-3-(pyridin-4-yl)-1-(pyrrolidin-1-yl)propan-2-ylcarbamate hydrochloride Compound 58

The compound was prepared according to method D with benzyl chloroformate (91 mg, 0.53 mmol). After work-up benzyl DL-threo-3-hydroxy-1-oxo-3-(pyridin-4-yl)-1-(pyrrolidin-1-yl)propan-2-ylcarbamate hydrochloride Compound 58 was obtained as a white solid (90 mg, 46% yield).

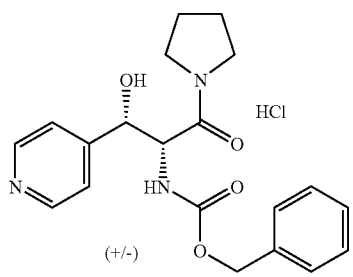

Compound 58

(+/-)

MW: 405.9; Yield: 46.0%; White Solid; Mp (° C.): 185.3. $R_f$: 0.38 (MeOH:EtOAc=10:90) free base.

1H-NMR (CD3OD, δ):: 1.87-2.03 (m, 4H, 2×CH$_2$), 3.40-3.48 (m, 2H, CH2N), 3.56-3.62 (m, 2H, CH2N), 4.85-5.04 (m, 3H, CH2O, CHO), 5.39 (d, 1H, J=2.8 Hz, NH), 7.26-7.36 (m, 5H, ArH), 8.12 (d, 2H, J=6.0 Hz, ArH), 8.69 (d, 2H, J=6.0 Hz, ArH).

$^{13}$C-NMR (CD$_3$OD, δ): δ 25.0, 27.0, 47.5, 48.0, 58.8, 67.9, 72.7, 126.6 (2×C), 129.1, 129.2, 129.5, 138.1, 141.9 (2×C), 158.1, 164.4, 169.2.

MS-ESI m/z (% rel. Int.): 370.1 ([MH]$^+$, 15), 219.0 (100).

HPLC: Method A, detection UV 254 nm, Compound 58 RT=4.10 min, peak area 99.8%.

trans-3-Methyl-5-pyridin-4-yl-4-(pyrrolidine-1-carbonyl)-oxazolidin-2-one hydrochloride Compound 70

To a stirred solution of DL-threo-3-hydroxy-1-oxo-3-(pyridin-4-yl)-1-(pyrrolidin-1-yl)propan-2-ylcarbamate Compound 58 free base (0.10 g, 0.27 mmol) in a mixture of DMSO:DMF (2 mL:0.2 mL) at 6° C. were added slowly tert-BuOK (38 mg, 0.33 mmol) and dimethyl sulfate (26 μL, 0.27 mmol). The mixture was stirred 15 h at RT under nitrogen and partitioned between ice water (5 mL), 1M Na2CO3 (2 mL) and ethyl acetate (100 mL). The organic phase was washed with brine (20 mL) and dried over MgSO4. After removing ethyl acetate by evaporation, the crude product was dried to give the crude free base as an oil. The hydrochloride salt was obtained in MeOH at 0° C. using a 0.3 M solution of HCl in diethylether. After precipitation in diethylether, trans-3-methyl-5-pyridin-4-yl-4-(pyrrolidine-1-carbonyl)-oxazolidin-2-one hydrochloride was obtained as a pale yellow solid (80 mg, 95% yield). A further crystallization in EtOAc:MeOH (10:1) gave Compound 70 as a white solid (16 mg, 20% yield).

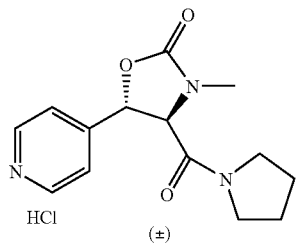

Compound 70

(±)

MW: 311.76; Yield: 20%; White Solid; Mp (° C.): 168.6. $R_f$: 0.15 (EtOAc:MeOH=95:5), free base.

1H-NMR (CD$_3$OD, δ): 1.90-2.10 (m, 4H, 2×CH$_2$), 2.84 (s, 3H, CH$_3$), 3.47-3.70 (m, 4H, CH$_2$N), 4.82 (m, 1H, CH), 5.89 (m, 1H, CH), 8.17 (m, 2H, ArH), 8.97 (m, 2H, ArH).

13C-NMR (CD$_3$OD, δ): 24.9, 27.1, 30.2, 48.1, 64.9, 76.3, 125.6 (2×C), 143.8 (2×C), 159.1, 160.1, 167.3.

MS-ESI m/z (% rel. Int.): 276.1 ([MH]+, 25), 177.1 (100).

HPLC: Method A, detection UV 254 nm, Compound 70 RT=2.00 min, peak area 97.0%.

What is claimed is:

1. A method for treating a cognitive disorder, the method comprising administering to a patient in need of such treatment a compound of the following structure:

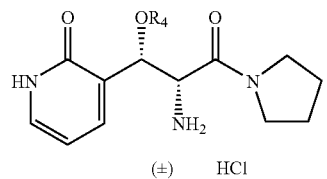

(±) HCl wherein $R_4$ is H, alkyl of 1 to 6 carbons or CO—$R_5$ wherein $R_5$ is alkyl of 1 to 6 carbons or any other pharmaceutically acceptable salt of said compound.

2. The method of claim 1, wherein $R_4$ is H.

* * * * *